US006523639B1

United States Patent
Shieh

(10) Patent No.: US 6,523,639 B1
(45) Date of Patent: Feb. 25, 2003

(54) RECEIVER STRUCTURE OF STETHOSCOPE

(76) Inventor: Woei-Kang Shieh, 4F, No. 63, HwaLin Street, ShihLin, Taipei City (TW)

(*) Notice: Subject to any disclaimer, the term of this patent is extended or adjusted under 35 U.S.C. 154(b) by 0 days.

(21) Appl. No.: 10/234,514

(22) Filed: Sep. 5, 2002

(51) Int. Cl.$^7$ .............................................. A61B 7/02
(52) U.S. Cl. ...................................................... 181/131
(58) Field of Search ................................ 181/131, 132, 181/135, 137, 155, 156; D24/134; 381/67; 600/528

(56) References Cited

U.S. PATENT DOCUMENTS 5,389,747 A * 2/1995 Mohrin ....................... 181/131
5,945,640 A * 8/1999 Rossini et al. .............. 181/131
5,945,641 A * 8/1999 Shieh ......................... 181/131

* cited by examiner

*Primary Examiner*—Robert E. Nappi
*Assistant Examiner*—Patrick Miller
(74) *Attorney, Agent, or Firm*—Bacon & Thomas, PLLC

(57) ABSTRACT

A receiver structure of stethoscope which can be switched back and forth between high- and low-frequency sound comprises a receiver body, a double-hoop frame, and a membrane, in which a groove is formed in an outer periphery of a sound-pickup cambered surface of the receiver body for buttoning up and assembling the double-hoop frame. The double-hoop frame further comprises an outer hoop and an inner hoop, which are supported by at least two links; and a gap is formed between the outer hoop and at least two links for clamping and fixing the rim of the membrane. When using a stethoscope of this kind, a large cavity would be formed and enclosed by the cambered surface, the outer hoop, and the membrane to enable a user to hear low-frequency sound via a pickup duct; or, a small cavity would be formed when the user depresses the receiver body harder to enable the user to hear high-frequency sound.

2 Claims, 6 Drawing Sheets

RECEIVER STRUCTURE OF STETHOSCOPE

FIELD OF THE INVENTION

The present invention relates generally to a receiver structure of stethoscope, and in particular to a receiver structure of stethoscope which can be switched back and forth between high- and low-frequency sound.

BACKGROUND OF THE INVENTION

A stethescope is an indispensable tool for a medical man to execute his job. A user may realize a patient's internal situations by means of the amplification function of the stethoscope together with his professional knowledge and experience to thereby make a correct diagnosis or take some other effective treatments.

Following to the remarkable progress in science technologies, many new electronic medical instruments have been developed to provide a better medical quality and accuracy, in which, nevertheless, the stethoscope is still an extremely important tool that any medical man always has to carry one with him whenever he is on duty.

A receiver of the stethoscope is arranged to collect and amplify the sound, for example, from an internal human organ in the event the receiver is put on somewhere of a patient's chest or abdomen. Then, the sound collected and amplified would go through the tubing and earplugs to reach the medical man's ears to provide very important information regarding the patient's illness or uncomfortableness. Moreover, an innovated stethoscope that can supply high and low audio frequencies for cross-reference is considered a powerful tool for diagnosis.

The related prior art has disclosed a "stethoscope structure" as shown in FIGS. 1 and 2. This stethoscope structure is constructed to provide high and low audio frequencies, in which a body of auscultation head (40) has a through hole (41); the through hole (41) has a high-frequency receiver (42) assembled therein; the high-frequency receiver (42) has a projecting depression member (43) at its external end and a circular flange (44) at its internal end; a supporting base (45) is assembled in the body of auscultation head (40); a large circular flange (46) is provided to the supporting base (45); a resilient member (47) is disposed between the supporting base (45) and the high-frequency receiver (42); and an acoustic board (48) is cup-jointed with a ferrule (49) and assembled on an external lateral face of the supporting base (45). When this stethoscope is put under use normally, the resilient member (47) is supposed to push and counterbalance the supporting base (45) such that the large circular flange (46) of the supporting base (45) would withstand and prop the acoustic board (48) to enable a user to listen to a low-frequency sound. When the depression member (43) is depressed as indicated in FIG. 2, the resilient member (47) is compressed to make the circular flange (44) of the high-frequency receiver (42) contact with the acoustic board (48). At this moment, the user is enabled to hear the high-frequency sound.

The prior patent can enable a user to listen to either a high-frequency sound or a low-frequency sound though, drawbacks are found including:

(a) Too many parts and too heavy weight;
(b) A too complicated structure, inconvenient switching between high and low sound, and a high breakdown rate; and
(c) A time-taken assembly job with high cost.

The stethoscope is a light, convenient, and low-cost tool that a medical man has to carry with him almost all the duty time as mentioned, however, in view of abovesaid defects of the priors, this invention is to provide an improved receiver structure of stethoscope which is advantageous in weight, simple architecture, and easy use.

SUMMARY OF THE INVENTION

A first objective of this invention is to provide a receiver structure of stethoscope, in which a large or a small cavity will be formed on a sound-pickup cambered surface of a receiver body by parting or gathering a membrane and a double-hoop frame for listening to low- or high-frequency sound dependent on the magnitude of an external force applied upon the membrane.

Another objective of this invention is to provide a receiver structure of stethoscope merited in lesser parts, lighter weight, simpler structure, and easier use.

Yet another objective of this invention is to provide a receiver structure of stethoscope merited in easier assembling and low cost.

In order to realize said objectives, a receiver structure of stethoscope of this invention mainly comprises a receiver body, a double-hoop frame, and a membrane, in which a groove is formed in an outer periphery of a pickup cambered surface of the receiver body for buttoning up and assembling the double-hoop frame. The double-hoop frame comprises an outer hoop and an inner hoop, in which the outer hoop is inwardly jointed with the inner hoop; the inner hoop would confront against the sound-pickup cambered surface; the outer and the inner hoops are supported by at least two links; a gap is formed between the outer hoop and at least those two links for clamping and fixing the rim of the membrane. When using a stethoscope of this kind, a user is supposed to tap the receiver body onto a patient to form a large cavity enclosed by the cambered surface, the outer hoop, and the membrane, so that the user can hear low-frequency sound via a pickup duct. Or, when the user depresses the receiver body harder to form a small cavity enclosed by the cambered surface, the inner hoop, and the membrane to enable the user to hear high-frequency sound.

For more detailed information regarding advantages or features of this invention, at least an example of preferred embodiment will be fully described below with reference to the annexed drawings.

BRIEF DESCRIPTION OF THE DRAWINGS

The related drawings in connection with the detailed description of this invention to be made later are described briefly as follows, in which.

DETAILED DESCRIPTION OF THE INVENTION

Figure 1:
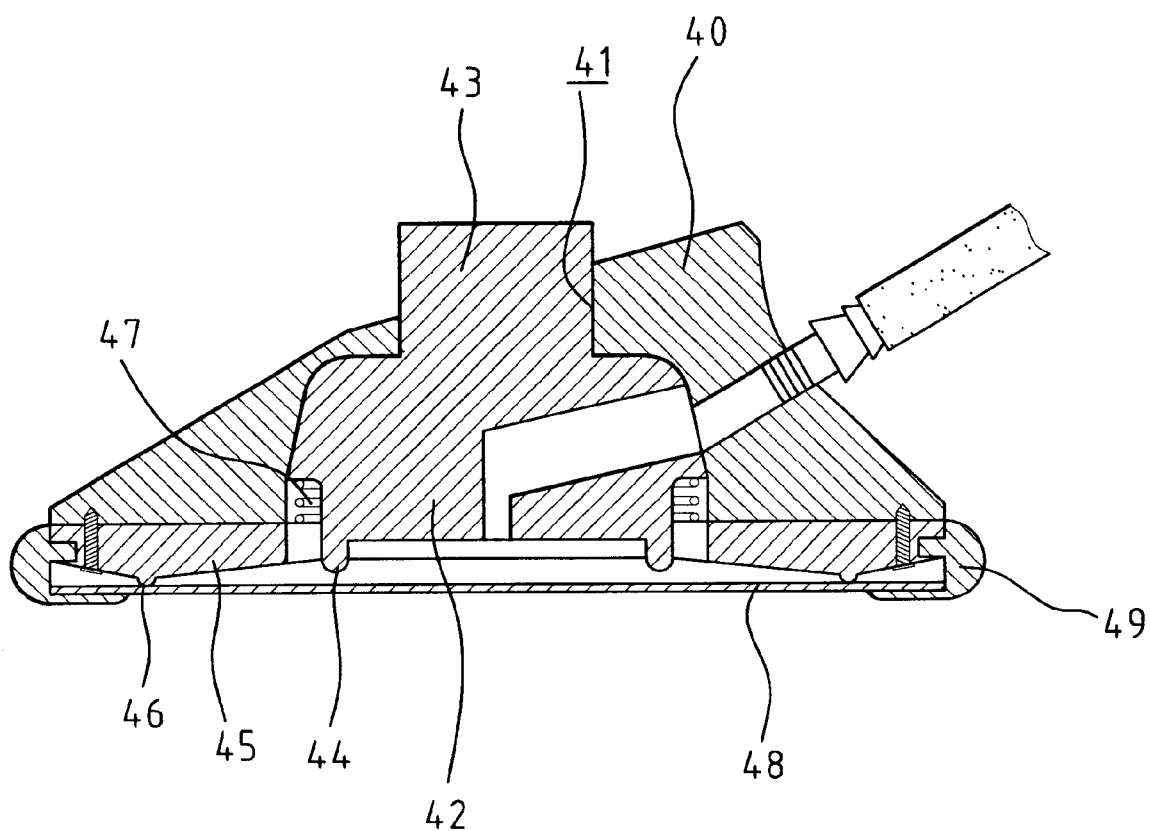
FIG. 1 is a cutaway sectional view of a conventional receiver structure of stethoscope under the state for listening to low-frequency sound.
Figure 2:
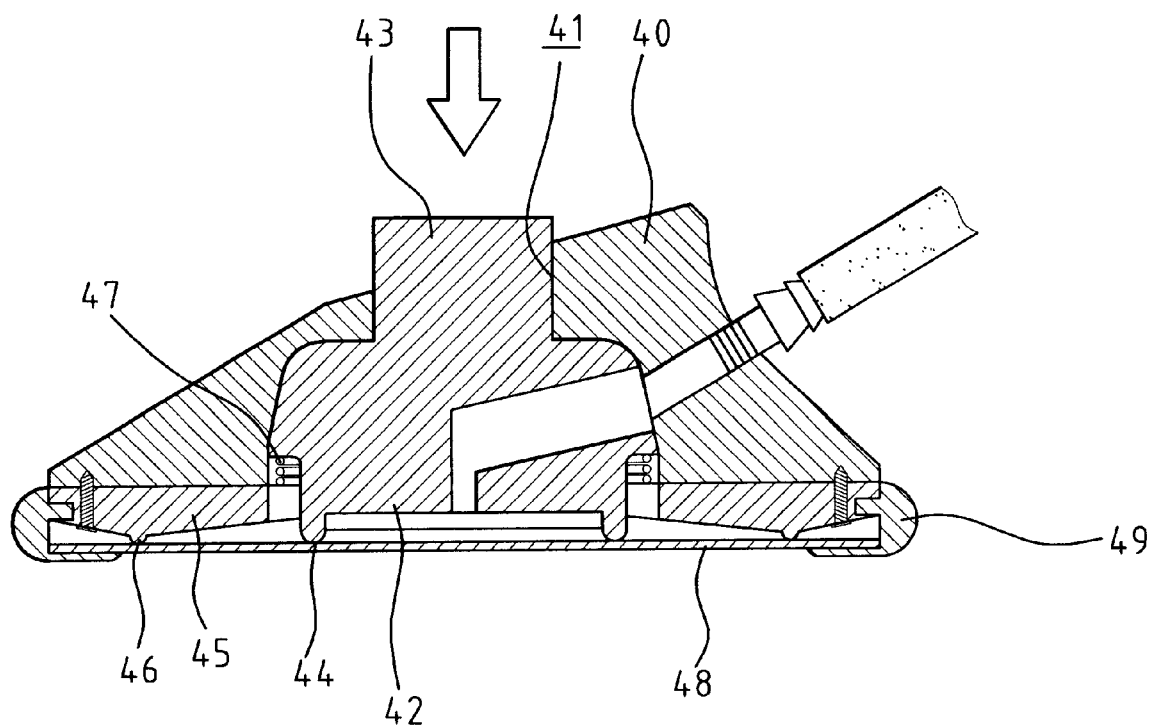
FIG. 2 is a cutaway sectional view of a conventional receiver structure of stethoscope under the state that a depression member is depressed for listening to high-frequency sound.
Figure 3:
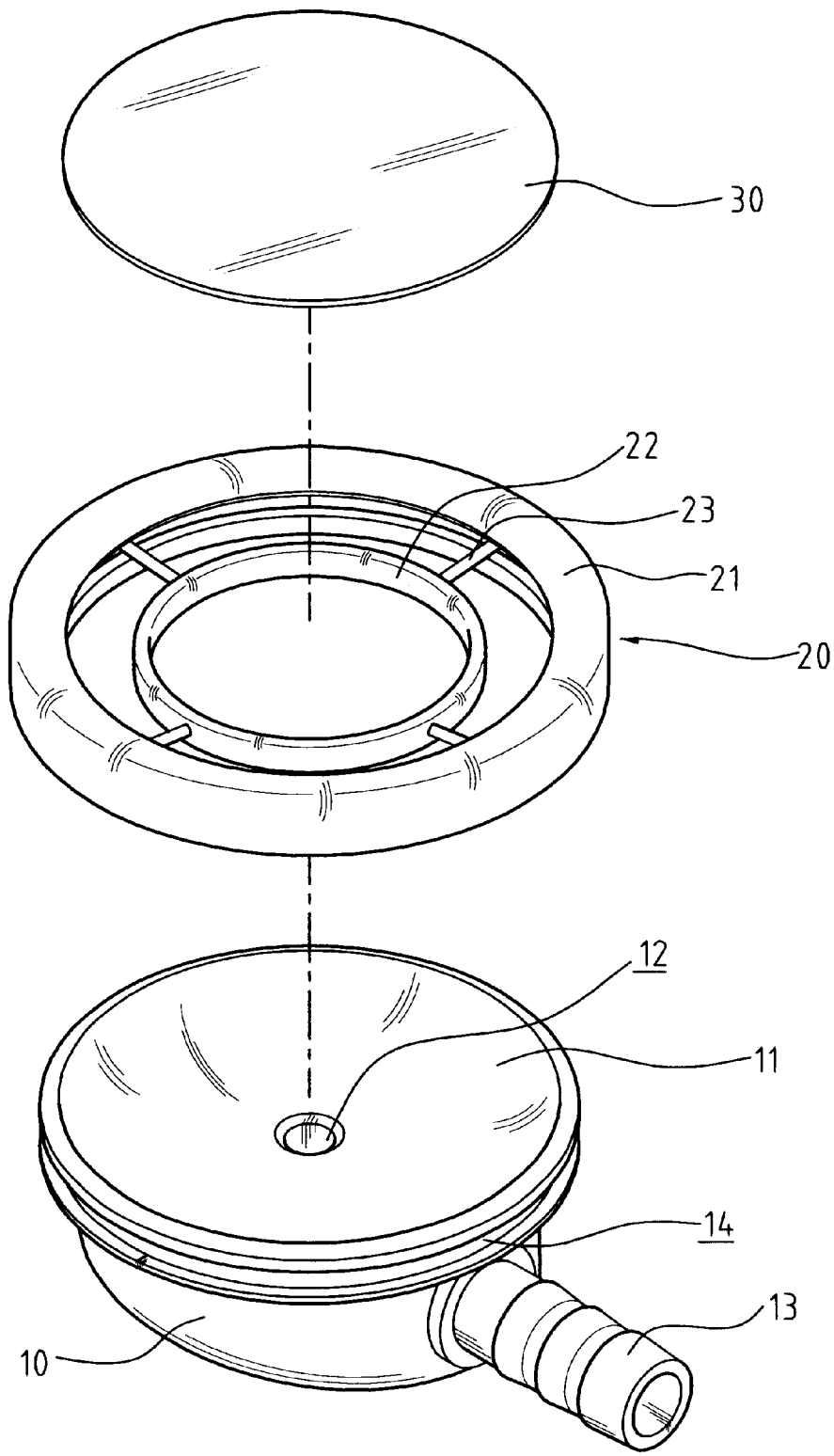
FIG. 3 is an exploded schematic view in three dimensions of an embodiment of this invention.
Figure 4:
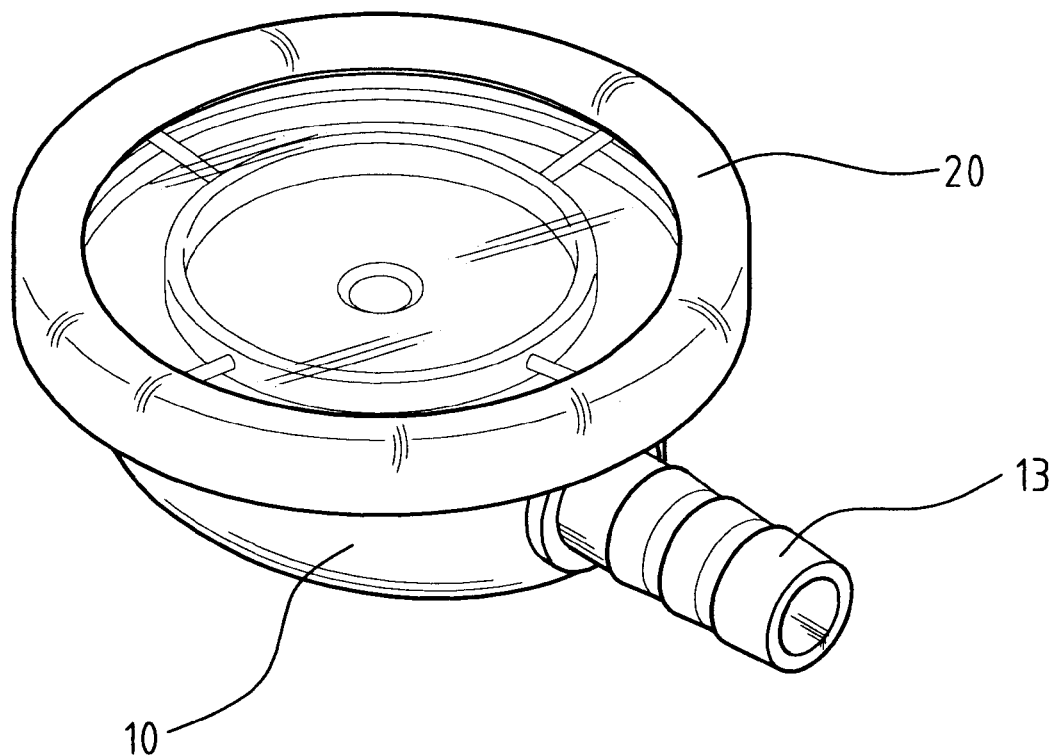
FIG. 4 is an assembled schematic view in three dimensions of an embodiment of this invention.
Figure 5:
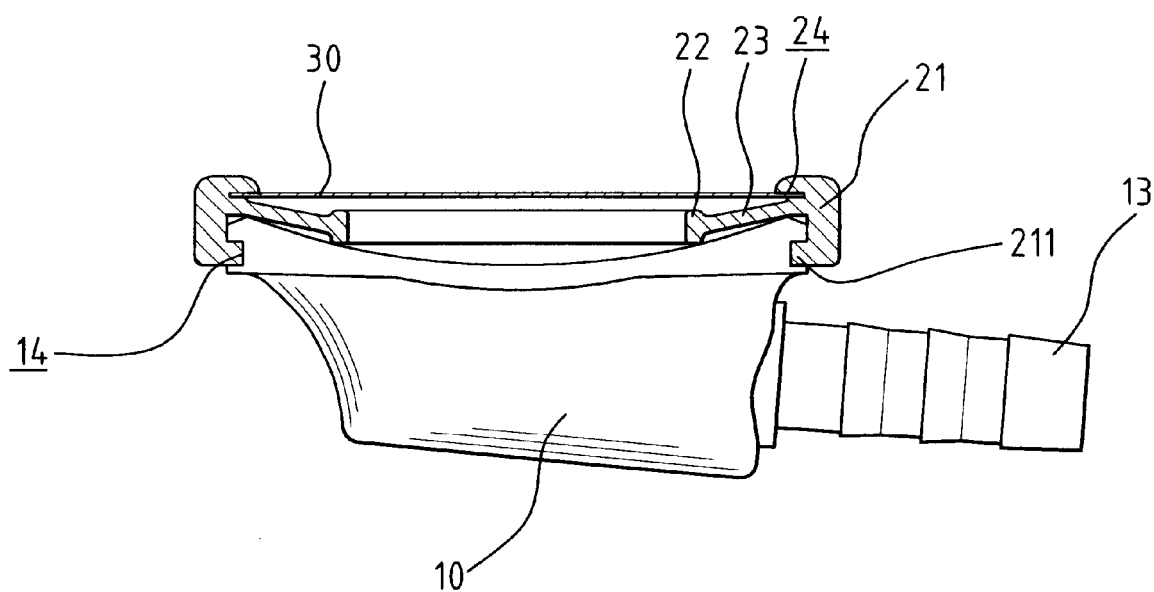
FIG. 5 is an assembled cutaway sectional view of an embodiment of this invention showing a state of listening to low-frequency sound.

An exploded view in three dimensions, an assembled view in three dimensions, and an assembled cutaway sectional view, of an embodiment of this invention are shown in FIGS. 3~5, respectively, in which a receiver structure of stethoscope mainly comprises: a receiver body (10), a double-hoop frame (20), and a membrane (30).

A sound-pickup cambered surface (11) of the receiver body (10) has a hole (12) interconnected with an outside sound-pickup duct (13) of the receiver body (10). A groove (14) is formed in an outer periphery of the pickup cambered surface (11) for buttoning up and assembling the double-hoop frame (20).

The double-hoop frame (20) consists of an outer hoop (21) and an inner hoop (22), in which a jutting ring (211) is arranged beneath the outer hoop (21) for snap-fastening the double-hoop frame to the groove (14) of the receiver body (10); at least two links (23) are employed to connect the outer hoop (21) with the inner hoop (22) that withstands downwardly against the pickup cambered surface (11); a gap (24) is formed between the outer hoop (21) and at least those two links (23) for clamping the rim of the membrane (30).

The membrane (30) is correspondent with the outer hoop (21) of the double-hoop frame (20) in shape, and the rim of the membrane (30) is larger than an inner edge of the outer hoop (21), so that the membrane (30) can be glazed in the gap (24) between the outer hoop (21) and at least those two links (23).

Figure 6:
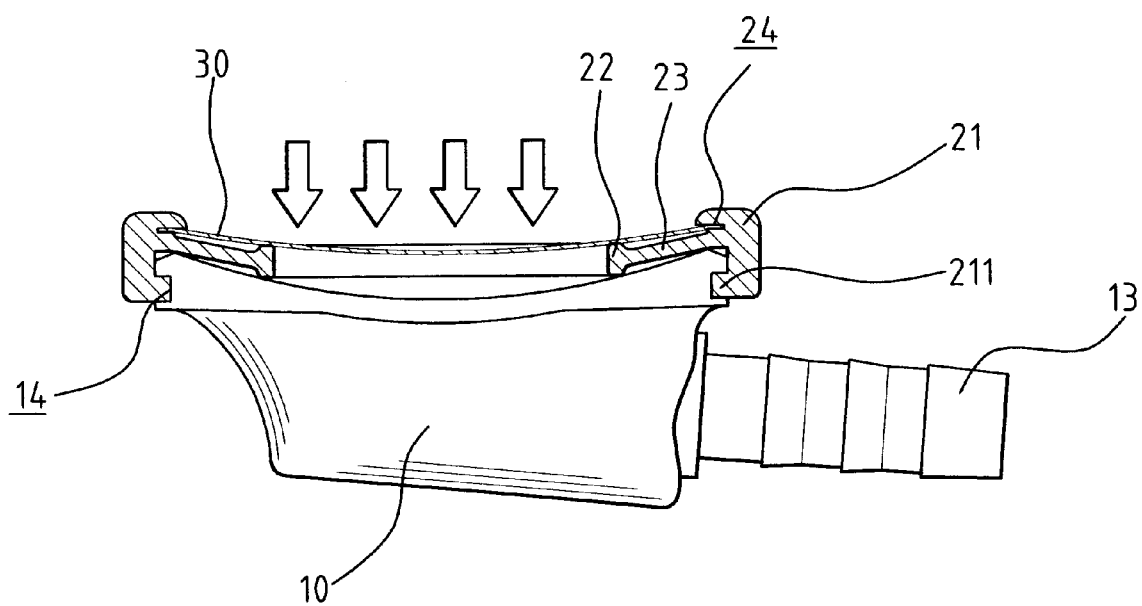
FIG. 6 is an assembled cutaway sectional view of an embodiment of this invention showing a membrane being depressed and deformed to touch an inner annular frame for listening to high-frequency sound.

When using a stethoscope of this kind, a user is supposed to tap the receiver body (10) onto a patient. At this time, a large cavity for sound pickup is formed and enclosed by the cambered surface (11), the outer hoop (21) of the double-hoop frame (20), and the membrane (30), so that the user can hear low-frequency sound via the pickup duct (13) as shown in FIG. 5. Or, when the user depresses the receiver body (10) harder as indicated in FIG. 6, the membrane (30) would be deformed inwardly to hence confront against the inner hoop (22) of the double-hoop frame (20) by a pressure from a touch portion of the patient. At this time, a small cavity enclosed by the cambered surface (11), the inner hoop (22) of the double-hoop frame (20), and the membrane (30) would enable the user to hear high-frequency sound.

As described above, a receiver structure of stethoscope of this invention is to perform its duty by means of parting or gathering the membrane (30) and the inner hoop (22) of the double-hoop frame (20) to thereby form a large or small cavity dependent on the magnitude of an external force applied upon the membrane (30), such that a user can hear low- or high-frequency sound with a simple operation. Therefore, it is understood that this invention is merited in simple construction, easy assembling, and low cost, and could be considered an innovated receiver structure of stethoscope.

In the above described, at least one preferred embodiment has been described in detail with reference to the drawings annexed, and it is apparent that numerous changes or modifications may be made without departing from the true spirit and scope thereof, as set forth in the claims below.

What is claimed is:

1. A receiver structure of stethoscope, comprising a receiver body, a double-hoop frame, and a membrane, in which a sound-pickup cambered surface of said receiver body has a hole interconnected to a sound-pickup duct outside said receiver body, and a groove is formed in the outer periphery of said cambered surface for snap-fastening and assembling said double-hoop frame;

said double-hoop frame is comprised of an outer hoop and an inner hoop supported by at least two links, in which a gap is formed between the outer hoop and at least those two links for clamping and fixing the rim of said membrane;

said membrane is correspondent with the outer hoop of said double-hoop frame in shape, and the rim of said membrane is larger than an inner edge of the outer hoop, so that the membrane can be glazed in the gap between the outer hoop and at least those two links; and when using a stethoscope of this kind, a large cavity for sound pickup is formed and enclosed by the cambered surface, the outer hoop of the double-hoop frame, and the membrane, so that a user is enabled to hear low-frequency sound via the pickup duct; or, when the user depresses the receiver body harder, the membrane would be deformed inwardly to hence confront against the inner hoop of the double-hoop frame, and at this time, a small cavity is enclosed by the cambered surface, the inner hoop, and the membrane to enable the user to hear high-frequency sound.

2. The receiver structure of stethoscope according to claim 1, in which a jutting ring is arranged beneath the outer hoop for snap-fastening said double-hoop frame to the groove of said receiver body.

* * * * *